US005728548A

United States Patent [19]
Bowman

[11] Patent Number: 5,728,548
[45] Date of Patent: Mar. 17, 1998

[54] RETINOID RECEPTOR-1 (RR1) AND DNA ENCODING RR1

[75] Inventor: Michael Bowman, Cambridge, Mass.

[73] Assignee: Genetics Institute, Inc., Cambridge, Mass.

[21] Appl. No.: 496,631

[22] Filed: Jun. 29, 1995

[51] Int. Cl.$^6$ .............................. C12P 21/00; C12N 15/11; C12N 5/16

[52] U.S. Cl. .................. 435/69.1; 435/325; 435/320.1; 435/252.3; 435/254.11; 536/23.5; 530/350; 514/12

[58] Field of Search .............................. 435/69.1, 240.2, 435/325, 320.1, 252.3, 254.11; 530/350; 536/23.1, 23.5; 514/2, 12

[56] References Cited

U.S. PATENT DOCUMENTS 5,317,090   5/1994   Blaudin De The et al. ........ 530/387.1

FOREIGN PATENT DOCUMENTS 9113167   9/1991   WIPO.
WO 94/07916   4/1994   WIPO.

OTHER PUBLICATIONS

Seol et al. (1995) Molecular Endocrinology 9:72–85.
Evans, Science 24:889 (1988).
Forman et al., Cell 81:687 (1995).
Green and Chambon, Nature 325:75 (1987).
Green and Chambon, TIG 4(11):309 (1988).

*Primary Examiner*—Stephen Walsh
*Assistant Examiner*—Michael D. Pak
*Attorney, Agent, or Firm*—Scott A. Brown; Thomas J. DesRosier

[57] ABSTRACT

Polynucleotides encoding retenoid receptor-1 (RR1) are disclosed. RR1 proteins and methods for their production, ligands for the RR1 and methods for their identification, and inhibitors of binding of RR1 and its ligands and methods for their identification are also disclosed.

20 Claims, 1 Drawing Sheet

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 2233 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 363..1778

( x i ) SEQUENCE DESCRIPTION: SEQ ID NO:1:

```
GAATTCGGCA  CGAGACTCTC  TCCTCCTCCT  CACCTCATTG  TCTCCCGAC   TTATCCTAAT      60

GCGAAATTGG  ATTCTGAGCA  TTTGTAGCAA  AATCGCTGGG  ATCTGGAGAG  GAAGACTCAG     120

TCCAGAATCC  TCCCAGGGCC  TTGAAAGTCC  ATCTCTGACC  CAAAACAATC  CAAGGAGGTA     180

GAAGACATCG  TAGAAGGAGT  GAAAGAAGAA  AAGAAGACTT  AGAAACATAG  CTCAAAGTGA     240
```

-continued

```
ACACTGCTTC TCTTAGTTTC CTGGATTTCT TCTGGACATT TCCTCAAGAT GAAACTTCAG        300

ACACTTTGGA GTTTTTTTTG AAGACCACCA TAAAGAAAGT GCATTCAAT TGAAAAATTT          360

GG ATG GGA TCA AAA ATG AAT CTC ATT GAA CAT TCC CAT TTA CCT ACC            407
   Met Gly Ser Lys Met Asn Leu Ile Glu His Ser His Leu Pro Thr
   1               5                  10                 15

ACA GAT GAA TTT TCT TTT TCT GAA AAT TTA TTT GGT GTT TTA ACA GAA           455
Thr Asp Glu Phe Ser Phe Ser Glu Asn Leu Phe Gly Val Leu Thr Glu
             20                  25                  30

CAA GTG GCA GGT CCT CTG GGA CAG AAC CTG GAA GTG GAA CCA TAC TCG           503
Gln Val Ala Gly Pro Leu Gly Gln Asn Leu Glu Val Glu Pro Tyr Ser
                 35                  40                  45

CAA TAC AGC AAT GTT CAG TTT CCC CAA GTT CAA CCA CAG ATT TCC TCG           551
Gln Tyr Ser Asn Val Gln Phe Pro Gln Val Gln Pro Gln Ile Ser Ser
             50                  55                  60

TCA TCC TAT TAT TCC AAC CTG GGT TTC TAC CCC CAG CAG CCT GAA GAG           599
Ser Ser Tyr Tyr Ser Asn Leu Gly Phe Tyr Pro Gln Gln Pro Glu Glu
65                  70                  75

TGG TAC TCT CCT GGA ATA TAT GAA CTC AGG CGT ATG CCA GCT GAG ACT           647
Trp Tyr Ser Pro Gly Ile Tyr Glu Leu Arg Arg Met Pro Ala Glu Thr
80                  85                  90                  95

CTC TAC CAG GGA GAA ACT GAG GTA GCA GAG ATG CCT GTA ACA AAG AAG           695
Leu Tyr Gln Gly Glu Thr Glu Val Ala Glu Met Pro Val Thr Lys Lys
                100                 105                 110

CCC CGC ATG GGC GCG TCA GCA GGG AGG ATC AAA GGG GAT GAG CTG TGT           743
Pro Arg Met Gly Ala Ser Ala Gly Arg Ile Lys Gly Asp Glu Leu Cys
             115                 120                 125

GTT GTT TGT GGA GAC AGA GCC TCT GGA TAC CAC TAT AAT GCA CTG ACC           791
Val Val Cys Gly Asp Arg Ala Ser Gly Tyr His Tyr Asn Ala Leu Thr
             130                 135                 140

TGT GAG GGG TGT AAA GGT TTC TTC AGG AGA AGC ATT ACC AAA AAC GCT           839
Cys Glu Gly Cys Lys Gly Phe Phe Arg Arg Ser Ile Thr Lys Asn Ala
145                 150                 155

GTG TAC AAG TGT AAA AAC GGG GGC AAC TGT GTG ATG GAT ATG TAC ATG           887
Val Tyr Lys Cys Lys Asn Gly Gly Asn Cys Val Met Asp Met Tyr Met
160                 165                 170                 175

CGA AGA AAG TGT CAA GAG TGT CGA CTA AGG AAA TGC AAA GAG ATG GGA           935
Arg Arg Lys Cys Gln Glu Cys Arg Leu Arg Lys Cys Lys Glu Met Gly
             180                 185                 190

ATG TTG GCT GAA TGC TTG TTA ACT GAA ATT CAG TGT AAA TCT AAG CGA           983
Met Leu Ala Glu Cys Leu Leu Thr Glu Ile Gln Cys Lys Ser Lys Arg
             195                 200                 205

CTG AGA AAA AAT GTG AAG CAG CAT GCA GAT CAG ACC GTG AAT GAA GAC          1031
Leu Arg Lys Asn Val Lys Gln His Ala Asp Gln Thr Val Asn Glu Asp
             210                 215                 220

AGT GAA GGT CGT GAC TTG CGA CAA GTG ACC TCG ACA ACA AAG TCA TGC          1079
Ser Glu Gly Arg Asp Leu Arg Gln Val Thr Ser Thr Thr Lys Ser Cys
225                 230                 235

AGG GAG AAA ACT GAA CTC ACC CCA GAT CAA CAG ACT CTT CTA CAT TTT          1127
Arg Glu Lys Thr Glu Leu Thr Pro Asp Gln Gln Thr Leu Leu His Phe
240                 245                 250                 255

ATT ATG GAT TCA TAT AAC AAA CAG AGG ATG CCT CAG GAA ATA ACA AAT          1175
Ile Met Asp Ser Tyr Asn Lys Gln Arg Met Pro Gln Glu Ile Thr Asn
             260                 265                 270

AAA ATT TTA AAA GAA GAA TTC AGT GCA GAA GAA AAT TTT CTC ATT TTG          1223
Lys Ile Leu Lys Glu Glu Phe Ser Ala Glu Glu Asn Phe Leu Ile Leu
             275                 280                 285

ACG GAA ATG GCA ACC AAT CAT GTA CAG GTT CTT GTA GAA TTC ACA AAA          1271
Thr Glu Met Ala Thr Asn His Val Gln Val Leu Val Glu Phe Thr Lys
             290                 295                 300
```

```
AAG CTA CCA GGA TTT CAG ACT TTG GAC CAT GAA GAC CAG ATT GCT TTG      1319
Lys Leu Pro Gly Phe Gln Thr Leu Asp His Glu Asp Gln Ile Ala Leu
    305             310                 315

CTG AAA GGG TCT GCG GTT GAA GCT ATG TTC CTT CGT TCA GCT GAG ATT      1367
Leu Lys Gly Ser Ala Val Glu Ala Met Phe Leu Arg Ser Ala Glu Ile
320             325                 330                 335

TTC AAT AAG AAA CTT CCG TCT GGG CAT TCT GAC CTA TTG GAA GAA AGA      1415
Phe Asn Lys Lys Leu Pro Ser Gly His Ser Asp Leu Leu Glu Glu Arg
                340                 345                 350

ATT CGA AAT AGT GGT ATC TCT GAT GAA TAT ATA ACA CCT ATG TTT AGT      1463
Ile Arg Asn Ser Gly Ile Ser Asp Glu Tyr Ile Thr Pro Met Phe Ser
                355                 360                 365

TTT TAT AAA AGT ATT GGG GAA CTG AAA ATG ACT CAA GAG GAG TAT GCT      1511
Phe Tyr Lys Ser Ile Gly Glu Leu Lys Met Thr Gln Glu Glu Tyr Ala
        370             375                 380

CTG CTT ACA GCA ATT GTT ATC CTG TCT CCA GAT AGA CAA TAC ATA AAG      1559
Leu Leu Thr Ala Ile Val Ile Leu Ser Pro Asp Arg Gln Tyr Ile Lys
        385             390                 395

GAT AGA GAG GCA GTA GAG AAG CTT CAG GAG CCA CTT CTT GAT GTG CTA      1607
Asp Arg Glu Ala Val Glu Lys Leu Gln Glu Pro Leu Leu Asp Val Leu
400             405                 410                 415

CAA AAG TTG TGT AAG ATT CAC CAG CCT GAA AAT CCT CAA CAC TTT GCC      1655
Gln Lys Leu Cys Lys Ile His Gln Pro Glu Asn Pro Gln His Phe Ala
                420                 425                 430

TGT CTC CTG GGT CGC CTG ACT GAA TTA CGG ACA TTC AAT CAT CAC CAC      1703
Cys Leu Leu Gly Arg Leu Thr Glu Leu Arg Thr Phe Asn His His His
                435                 440                 445

GCT GAG ATG CTG ATG TCA TGG AGA GTA AAC GAC CAC AAG TTT ACC CCA      1751
Ala Glu Met Leu Met Ser Trp Arg Val Asn Asp His Lys Phe Thr Pro
        450                 455                 460

CTT CTC TGT GAA ATC TGG GAC GTG CAG TGATGGGGAT TACAGGGGAG            1798
Leu Leu Cys Glu Ile Trp Asp Val Gln
        465                 470

GGGTCTAGCT CCTTTTTCTC TCTCATATTA ATCTGATGTA TAACTTTCCT TTATTTCACT    1858

TGTACCCAGT TTCACTCAAG AAATCTTGAT GAATATTTAT GTTGTAATTA CATGTGTAAC    1918

TTCCACAACT GTAAATATTG GGCTAGATAG AACAACTTTC TCTACATTGT GTTTTAAAAG    1978

GCTCCAGGGA ATCCTGCATT CTAATTGGCA AGCCCTGTTT GCCTAATTAA ATTGATTGTT    2038

ACTTCAATTC TATCTGTTGA ACTAGGGAAA ATCTCATTTT GCTCATCTTA CCATATTGCA    2098

TATATTTTAT TAAAGAGTTG TATTCAATCT TGGCAATAAA GCAAACATAA TGGCAACAGA    2158

AAAAAAAAAA AAAAAAAAAA AAAAAAAAAA AAAAAAAAAA AAAAAAAAAA AAAAAAAAAA    2218

AAAAAAAAAC TCGAG                                                     2233
```

( 2 ) INFORMATION FOR SEQ ID NO:2:

( i ) SEQUENCE CHARACTERISTICS:
        ( A ) LENGTH: 472 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Gly Ser Lys Met Asn Leu Ile Glu His Ser His Leu Pro Thr Thr
1               5                   10                  15

Asp Glu Phe Ser Phe Ser Glu Asn Leu Phe Gly Val Leu Thr Glu Gln
                20                  25                  30

Val Ala Gly Pro Leu Gly Gln Asn Leu Glu Val Glu Pro Tyr Ser Gln
```

|  | 35 |  |  |  | 40 |  |  |  | 45 |  |  |  |
|---|---|---|---|---|---|---|---|---|---|---|---|---|

Tyr Ser Asn Val Gln Phe Pro Gln Val Gln Pro Gln Ile Ser Ser Ser
50                   55                  60

Ser Tyr Tyr Ser Asn Leu Gly Phe Tyr Pro Gln Gln Pro Glu Glu Trp
65               70                  75                  80

Tyr Ser Pro Gly Ile Tyr Glu Leu Arg Arg Met Pro Ala Glu Thr Leu
                85                  90                  95

Tyr Gln Gly Glu Thr Glu Val Ala Glu Met Pro Val Thr Lys Lys Pro
            100                 105                 110

Arg Met Gly Ala Ser Ala Gly Arg Ile Lys Gly Asp Glu Leu Cys Val
            115                 120                 125

Val Cys Gly Asp Arg Ala Ser Gly Tyr His Tyr Asn Ala Leu Thr Cys
    130                 135                 140

Glu Gly Cys Lys Gly Phe Phe Arg Arg Ser Ile Thr Lys Asn Ala Val
145                 150                 155                 160

Tyr Lys Cys Lys Asn Gly Gly Asn Cys Val Met Asp Met Tyr Met Arg
                165                 170                 175

Arg Lys Cys Gln Glu Cys Arg Leu Arg Lys Cys Lys Glu Met Gly Met
            180                 185                 190

Leu Ala Glu Cys Leu Leu Thr Glu Ile Gln Cys Lys Ser Lys Arg Leu
        195                 200                 205

Arg Lys Asn Val Lys Gln His Ala Asp Gln Thr Val Asn Glu Asp Ser
    210                 215                 220

Glu Gly Arg Asp Leu Arg Gln Val Thr Ser Thr Thr Lys Ser Cys Arg
225                 230                 235                 240

Glu Lys Thr Glu Leu Thr Pro Asp Gln Gln Thr Leu Leu His Phe Ile
                245                 250                 255

Met Asp Ser Tyr Asn Lys Gln Arg Met Pro Gln Glu Ile Thr Asn Lys
            260                 265                 270

Ile Leu Lys Glu Glu Phe Ser Ala Glu Glu Asn Phe Leu Ile Leu Thr
        275                 280                 285

Glu Met Ala Thr Asn His Val Gln Val Leu Val Glu Phe Thr Lys Lys
    290                 295                 300

Leu Pro Gly Phe Gln Thr Leu Asp His Glu Asp Gln Ile Ala Leu Leu
305                 310                 315                 320

Lys Gly Ser Ala Val Glu Ala Met Phe Leu Arg Ser Ala Glu Ile Phe
                325                 330                 335

Asn Lys Lys Leu Pro Ser Gly His Ser Asp Leu Leu Glu Glu Arg Ile
            340                 345                 350

Arg Asn Ser Gly Ile Ser Asp Glu Tyr Ile Thr Pro Met Phe Ser Phe
        355                 360                 365

Tyr Lys Ser Ile Gly Glu Leu Lys Met Thr Gln Glu Glu Tyr Ala Leu
    370                 375                 380

Leu Thr Ala Ile Val Ile Leu Ser Pro Asp Arg Gln Tyr Ile Lys Asp
385                 390                 395                 400

Arg Glu Ala Val Glu Lys Leu Gln Glu Pro Leu Leu Asp Val Leu Gln
                405                 410                 415

Lys Leu Cys Lys Ile His Gln Pro Glu Asn Pro Gln His Phe Ala Cys
            420                 425                 430

Leu Leu Gly Arg Leu Thr Glu Leu Arg Thr Phe Asn His His His Ala
        435                 440                 445

Glu Met Leu Met Ser Trp Arg Val Asn Asp His Lys Phe Thr Pro Leu
    450                 455                 460

Leu Cys Glu Ile Trp Asp Val Gln
465                     470

( 2 ) INFORMATION FOR SEQ ID NO:3:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

TTTTTTTTTT TTMC                                      14

( 2 ) INFORMATION FOR SEQ ID NO:4:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

AUUUAUUUAU UUA                                      13

( 2 ) INFORMATION FOR SEQ ID NO:5:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

TTATTTAAA                                                9

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

GTCAGAAAAA TTTAATTTA GG                          22

( 2 ) INFORMATION FOR SEQ ID NO:7:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

AAATACAGTT TGCTTATGAA AG                          22

RETINOID RECEPTOR-1 (RR1) AND DNA ENCODING RR1

FIELD OF THE INVENTION

The present invention relates to steroid receptor proteins, nucleic acids encoding such proteins, ligands thereto and methods of identifying inhibitors of activity of such proteins.

BACKGROUND OF THE INVENTION

The steroid receptor superfamily is a class of protein receptors which interact with specific DNA sequences and modulate gene expression in response to the binding of retinoids, steroids, thyroid hormones and other molecules (Berg, Cell, 57: 1065–1068 (1989); Evans, Science, 240:889–895 (1989)). Members of the superfamily demonstrate substantial sequence conservation in two functional regions. The highest level of conservation is observed in the "C box" region, which contains nine cysteine residues which are capable of binding zinc to form "zinc fingers," which interact with the cognate steroid response elements of DNA (Miller et al., EMBO J., 4:1609–1614 (1985); Evans, Cell, 52:1–3 (1988)). Substantial conservation is also observed in the "E box" or ligand binding domain of these receptors (Carlstedt-Duke et al., Proc. Natl. Acad. Sci. U.S.A., 79:4260–4264 (1982); Carlstedt-Duke et al., Proc. Natl. Acad. Sci. U.S.A., 84:4437–4440 (1982)). Additional functional domains of members of the superfamily have also been identified, including protein-protein interaction sites that participate in transcriptional regulation (Scule et al., Cell, 62:1217–1226 (1990); Yang, Cell, 62:1205–1215 (1990); Holloway et at., Proc. Natl. Acad. Sci. U.S.A., 87:8160–8164 (1990)).

Several members of the superfamily have been identified on the basis of sequence conservation, including: hER1 and hER2 (Giguere et at., Nature, 331:91–94 (1988)); and retinoic acid receptors and the peroxisome proliferative activator receptor (PPAR) (Issemann et al., Nature, 345:224–229 (1990)). Three members of the Xenopus nuclear hormone receptor have also been disclosed (Dreyer, Cell, 68:879–887 (1992)). U.S. Pat. No. 4,981,784 to Evans et al. discloses the identification of a retinoic acid receptor and the use of chimeric constructs to produce hybrid receptors for the identification of novel ligands.

It would be desirable to identify and to isolate additional members of this receptor superfamily and to identify the ligands binding thereto.

SUMMARY OF THE INVENTION

In accordance with the present invention, polynucleotides encoding novel steroid receptors and novel steroid receptor proteins are disclosed. The novel receptor has been designated "hRRI" (human retinoid receptor-i). "RRI" is used throughout the present specification to refer to both receptor proteins and polynucleotides encoding those proteins and to refer to proteins and polynucleotides from all mammalian species.

In certain embodiments, the present invention provides for an isolated polynucleotide comprising a nucleotide sequence selected from the group consisting of: (a) the nucleotide sequence of SEQ ID NO:1 from nucleotide 363 to nucleotide 1778; (b) a nucleotide sequence capable of hybridizing under highly stringent, stringent or relaxed conditions to a nucleic acid sequence specified in (a); (c) a nucleotide sequence varying from the sequence of the nucleotide sequence specified in (a) as a result of degeneracy of the genetic code; and (d) an allelic variant of the nucleotide sequence specified in (a). In particular embodiments, the nucleotide sequence encodes for protein having RR1 DNA-binding activity and/or RR1 ligand binding activity. Polynucleotides encoding various mammalian RR1 proteins (including murine and human RR1 proteins) are included in the present invention. In other embodiments, the nucleotide sequence is operably linked to an expression control sequence.

The present invention also encompasses host cells transformed with the polynucleotide of the invention, including mammalian cells.

In other embodiments, the invention provides for a process for producing an RR1 protein, said process comprising: (a) growing a culture of host cells transformed with a polynucleotide of the invention in a suitable culture medium; and (b) purifying the RR1 protein from the culture. RR1 protein produced by such methods is also provided by the present invention.

Further embodiments of the present invention provide isolated RR1 protein comprising an amino acid sequence selected from the group consisting of: (a) the amino acid sequence of SEQ ID NO:2; (b) fragments of (a) having RR1 DNA-binding activity; and (c) fragments of (a) having RR1 ligand binding activity. Pharmaceutical compositions comprising RR1 protein and a pharmaceutically acceptable carrier are also contemplated by the present invention, as are compositions comprising antibodies (polyclonal and monoclonal) which specifically react with RR1 protein. Polynucleotides encoding each of these proteins are also provided by the present invention.

The present invention also encompasses methods of identifying an RR1 ligand, said method comprising: (a) providing a sample containing a potential source of RR1 ligand; (b) contacting said sample with a protein having RR1 DNA-binding activity or RR1 ligand binding activity; and (c) collecting materials binding to the protein. RR1 ligands identified according to the method of the present invention and pharmaceutical compositions comprising such ligands are also provided.

The invention also provides for methods of treating various medical conditions, methods of inhibiting binding of an RR1 ligand to an RR1 protein, and methods of inhibiting binding of an RR1 protein to DNA by administering to a mammalian subject a therapeutically effective amount of a pharmaceutical composition comprising an RR1 protein or ligand, an antibody to either molecule or another peptide or small molecule inhibitor of binding.

In another embodiment, the invention provides a method of identifying an inhibitor of DNA binding to RR1 protein which comprises: (a) combining an RR1 protein with DNA which binds to the receptor protein, said combination forming a first binding mixture; (b) measuring the amount of binding between the RR1 protein and the DNA in the first binding mixture; (c) combining a compound with the RR1 protein and the DNA to form a second binding mixture; (d) measuring the amount of binding in the second binding mixture; and (e) comparing the amount of binding in the first binding mixture with the amount of binding in the second binding mixture; wherein the compound is capable of inhibiting DNA binding to RR1 protein when a decrease in the amount of binding of the second binding mixture occurs.

In another embodiment, the invention provides a method of identifying an inhibitor of ligand binding to RR1 protein which comprises: (a) combining an RR1 protein with a ligand, said combination forming a first binding mixture; (b) measuring the amount of binding between the RR1 protein and the RR1 binding ligand in the first binding mixture; (c) combining a compound with the RR1 protein and the ligand to form a second binding mixture; (d) measuring the amount of binding in the second binding mixture; and (e) comparing the amount of binding in the first binding mixture with the amount of binding in the second binding mixture; wherein the compound is capable of inhibiting ligand binding to RR1 protein when a decrease in the amount of binding of the second binding mixture occurs.

Inhibitors identified according to these methods, pharmaceutical compositions comprising such inhibitor and methods of treatment employing such compositions are also provided by the present invention.

DETAILED DESCRIPTION OF PREFERRED EMBODIMENTS

Figure 1:
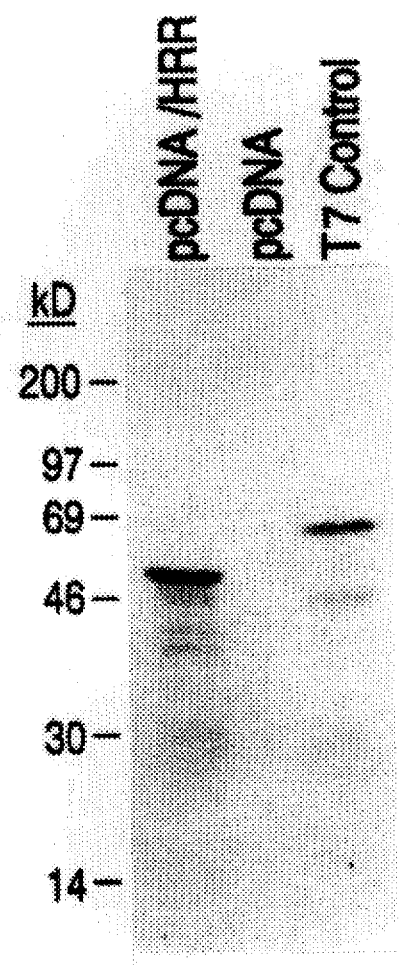
FIG. 1 depicts a gel demonstrating expression of hRR1.

The inventors of the present application have identified and provided a polynucleotide encoding a novel steroid receptor designated "hRR1". SEQ ID NO:1 provides the nucleotide sequence of a cDNA encoding the human RR1 protein. SEQ ID NO:2 provides the amino acid sequence of the human RR1.

The hRR1 has at least four putative domains which are characteristic of steroid receptor: an "AB box" (comprising approximately amino acids 1–126 of SEQ ID NO:2), a "C box" or "zinc finger" domain (comprising approximately amino acids 127–192 of SEQ ID NO:2), a "D box" (comprising approximately amino acids 193–256 of SEQ ID NO:2) and an "E box" or ligand binding domain (comprising approximately amino acids 257–470 of SEQ ID NO:2). The hRR1 does not appear to contain an "F box" found in many steroid receptors.

RR1 proteins comprising only one or several domains or portions thereof may also be produced. Any forms of RR1 protein of less than full length are encompassed within the present invention and may be produced by expressing a corresponding fragment of the polynucleotide encoding the RR1 protein (such as SEQ ID NO:1). These corresponding polynucleotide fragments are also part of the present invention. Modified polynucleotides as described above may be made by standard molecular biology techniques, including site-directed mutagenesis methods which are known in the art or by the polymerase chain reaction using appropriate oligonucleotide primers.

Chimeric RR1 proteins may also be constructed in which one or more domains of RR1 are linked to one or more domains of another steroid hormone receptor protein (such as glucocorticoid receptor protein, thyroid receptor protein, mineral-ocorticoid receptor protein or retinoic acid receptor protein). Preferred chimeric molecules include those in which the ligand binding domain of RR1 is linked to the DNA binding domain of another receptor. These chimeric molecules are particularly useful for identification of ligands to RR1. They may be employed in assays which can detected RR1 ligand binding. In suitable assays, a hormone response element (wild type or engineered) which is capable of being activated by the DNA-binding domain of the chimeric molecule is operably linked to a reporter gene (such as the CAT gene or the firefly luciferase gene) such that interaction of the chimera with the response element produces signal by expression of the reporter gene. Host cells transfected with the chimeric construct and the response element/reporter gene construct can then be exposed to ligand sources and operative ligand candidates can be identified.

For the purposes of the present invention, a protein has "RR1 DNA-binding activity" when it is capable of binding to asteroid receptor DNA binding site and initiating transcription of a reporter gene as measured by an appropriate assay. A protein has "RR1 ligand binding activity" when it binds RR1 ligand as measured by a suitable ligand binding assay. Activity of an RR1 protein can be measured by incorporating such protein into a chimeric receptor (i.e., a combination with a portion of another receptor) to determine its activity. For example, an RR1 protein can be tested for RR1 DNA-binding activity by combining it with the ligand binding portion of a second steroid receptor and its ability to bind DNA and initiate transcription in the presence of the ligand can be observed. Similarly, an RR1 protein can be tested for RR1 ligand binding activity by combination with the DNA-binding domain of a second receptor and testing for initiation in the presence of an RR1 ligand. Suitable procedures include those described by Green et at., Nature, 325:75–78 (1987) and other similar assays known in the art which employ luciferase as a reporter.

RR1 protein or fragments thereof having RR1 ligand binding activity may be fused to carrier molecules such as immunoglobulins. For example, RR1 protein containing the E box may be fused through "linker" sequences to the Fc portion of an immunoglobulin.

The invention also encompasses allelic variations of the nucleotide sequence as set forth in SEQ ID NO:1, that is, naturally-occurring alternative forms of the isolated polynucleotide of SEQ ID NO:1 which also encode proteins having RR1 DNA-binding activity or RR1 ligand binding activity. Also included in the invention are isolated polynucleotides which hybridize to the nucleotide sequence set forth in SEQ ID NO:1 under highly stringent (0.2×SSC at 65° C.), stringent (e.g. 4×SSC at 65° C. or 50% formamide and 4×SSC at 42° C.), or relaxed (4×SSC at 50° C. or 30–40% formamide at 42° C.) conditions. Isolated polynucleotides which encode RR1 protein but which differ from the nucleotide sequence set forth in SEQ ID NO:1 by virtue of the degeneracy of the genetic code are also encompassed by the present invention. Variations in the nucleotide sequence as set forth in SEQ ID NO:1 which are caused by point mutations or by induced modifications which enhance RR1 DNA-binding activity or RR1 ligand binding activity, half-life or production level are also included in the invention.

The isolated polynucleotides of the invention may be operably linked to an expression control sequence such as the pMT2 or pED expression vectors disclosed in Kaufman et al., Nucleic Acids Res. 19, 4485–4490 (1991), in order to produce the RR1 protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means enzymatically or chemically ligated to form a covalent bond between the isolated polynucleotide of the invention and the expression control sequence, in such a way that the RR1 protein is expressed by a host cell which has been transformed (transfected) with the ligated polynucleotide/expression control sequence.

A number of types of cells may act as suitable host cells for expression of the RR1 protein. Any cell type capable of expressing functional RR1 protein may be used. Suitable mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK, Rat2, BaF3, 32D, FDCP-1, PC12 or C2C12 cells.

The RR1 protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, Texas Agricultural Experiment Station Bulletin No. 1555 (1987), incorporated herein by reference. Soluble forms of the RR1 protein may also be produced in insect cells using appropriate isolated polynucleotides as described above.

Alternatively, the RR1 protein may be produced in lower eukaryotes such as yeast or in prokaryotes such as bacteria. Suitable yeast strains include Saccharomyces cerevisiae, Schizosaccharomyces pombe, Kluyveromyces strains, Candida, or any yeast strain capable of expressing heterologous proteins. Suitable bacterial strains include *Escherichia coli, Bacillus subtilis, Salmonella typhimurium*, or any bacterial strain capable of expressing heterologous proteins.

The RR1 protein of the invention may also be expressed as a product of transgenic animals, e.g., as a component of the milk of transgenic cows, goats, pigs, or sheep which are characterized by somatic or germ cells containing a polynucleotide sequence encoding the RR1 protein.

The RR1 protein of the invention may be prepared by growing a culture transformed host cells under culture conditions necessary to express the desired protein. The resulting expressed protein may then be purified from the culture medium or cell extracts. Soluble forms of the RR1 protein of the invention can be purified from conditioned media. Membrane-bound forms of RR1 protein of the invention can be purified by preparing a total membrane fraction from the expressing cell and extracting the membranes with a non-ionic detergent such as Triton X-100.

The RR1 protein can be purified using methods known to those skilled in the art. For example, the RR1 protein of the invention can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred (e.g., S-Sepharose® columns). The purification of the RR1 protein from culture supernatant may also include one or more column steps over such affinity resins as concanavalin A-agarose, heparin-toyopearl® or Cibacrom blue 3CA Sepharose®; or by hydrophobic interaction chromatography using such resins as phenyl ether, butyl ether, or propyl ether; or by immunoaffinity chromatography. Finally, one or more reverse-phase high performance liquid chromatography (RP-HPLC) steps employing hydrophobic RP-HPLC media, e.g., silica gel having pendant methyl or other aliphatic groups, can be employed to further purify the RR1 protein. Some or all of the foregoing purification steps, in various combinations or with other known methods, can also be employed to provide a substantially purified isolated recombinant protein.

Preferably, the isolated RR1 protein is purified so that it is substantially free of other mammalian proteins.

RR1 proteins of the present invention may also be used to identify and isolate RR1 ligands. Methods for doing so are known to those skilled in the art. For example, RR1 proteins having RR1 ligand binding activity may be anchored to a solid support (such as in a microtiter plate or a binding affinity column) and exposed to possible sources of RR1 ligands. Alternatively, a DNA containing response element could be anchored to a solid support and exposed to RR1 and a source of ligand. Species binding to the RR1 protein can then be eluted from the RR1 protein and collected for further characterization. Sources of RR1 ligands include among others liver, kidney, adrenal gland and fetal spleen and conditioned media from cell lines derived from these sources. RR1 ligands can also be identified by transactivation assays using a suitable reporter gene, such as CATm luciferase or β-galactosidase. RR1 ligands may also be used in pharmaceutical compositions as described above with respect to the RR1 protein.

The invention also includes ligands which bind to the RR1 ("RR1 ligands"). The ligands may be molecules that occur naturally in a mammal (either the same mammal or a different mammal from which the RR1 to which the ligand binds was isolated). The ligand may also be a molecule that does not occur naturally in a mammal.

RR1 protein of the invention may also be used to screen for agents which are capable of binding to RR1 protein (either the ligand binding or DNA binding domains) and thus may act as inhibitors of normal ligand or DNA binding. Binding assays are well known in the art and may be used for this purpose using the RR1 protein of the invention. Purified cell based or protein based (cell free) screening assays may be used to identify such agents. For example, RR1 protein may be mobilized in purified form on a carrier and binding to purified RR1 protein may be measured in the presence and in the absence of potential inhibiting agents. Any RR1 protein exhibiting RR1 ligand binding activity or DNA binding activity may be used in the screening assays described above.

In such a screening assay, a first binding mixture is formed by combining an RR1 protein with either ligand or DNA, and the amount of binding in the first binding mixture ($B_o$) is measured. A second binding mixture is also formed by those components and the compound or agent to be screened, and the amount of binding in the second binding mixture (B) is measured. The amounts of binding in the first and second binding mixtures are compared, for example, by performing a $B/B_o$ calculation. A compound or agent is considered to be capable of inhibiting binding if a decrease in binding in the second binding mixture as compared to the first binding mixture is observed. The formulation and optimization of binding mixtures is within the level of skill in the art, such binding mixtures may also contain buffers and salts necessary to enhance or to optimize binding, and additional control assays may be included in the screening assay of the invention.

Compounds found to reduce the binding activity of RR1 protein to ligand or DNA to any degree, preferably by at least about 10%, more preferably greater than about 50 % or more, may thus be identified and then secondarily screened in other binding assays and in vivo assays. By these means compounds having inhibitory activity for RR1 binding which may be suitable as therapeutic agents may be identified.

RR1 proteins and RR1 ligands are useful for identification of steroid hormone agonists and antagonists. RR1 proteins and RR1 ligands may also be useful in treatment of various medical conditions in which the RR1 is implicated or which are effected by the activity (or lack thereof) of RR1 (collectively "RR1-related conditions"). RR1-related conditions include without limitation adrenal deficiencies (such as Addison disease), cancers and tumors, skin disorders (such as acne and psoriasis), inflammatory disorders (such as arthritis), HIV infection and associated syndromes and to regulate an immune response (such as antitumor applications, as a vaccine adjuvant, as an inhibitor of organ rejection, and treatment of autoimmune conditions).

Isolated RR1 proteins and RR1 ligands, purified from cells or recombinantly produced, may be used as a pharmaceutical composition when combined with a pharmaceutically acceptable carrier. Such a composition may contain, in addition to RR1 protein or ligand and carrier, diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, IL-1, IL-2, IL-3, IL-4, IL-5, IL-6, IL-7, IL-8, IL-9, IL-10, IL-11, IL-12, IL-15, G-CSF, stem cell factor, and erythropoietin. The pharmaceutical composition may contain thrombolytic or anti-thrombotic factors such as plasminogen activator and Factor VIII. The pharmaceutical composition may further contain other anti-inflammatory agents. Such additional factors and/or agents may be included in the pharmaceutical composition to produce a synergistic effect with isolated RR1 protein or ligand, or to minimize side effects caused by the isolated RR1 protein or ligand. Conversely, isolated RR1 protein may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

The pharmaceutical composition of the invention may be in the form of a liposome in which isolated RR1 protein or ligand is combined, in addition to other pharmaceutically acceptable carriers, with amphipathic agents such as lipids which exist in aggregated form as micelles, insoluble monolayers, liquid crystals, or lamellar layers which in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

As used herein, the term "therapeutically effective amount" means the total amount of each active component of the pharmaceutical composition or method that is sufficient to show a meaningful patient benefit, e.g., amelioration of symptoms of, healing of, or increase in rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of isolated RR1 protein or ligand is administered to a mammal. Isolated RR1 protein or ligand may be administered in accordance with the method of the invention either alone or in combination with other therapies such as treatments employing cytokines, lymphokines or other hematopoietic factors. When co-administered with one or more cytokines, lymphokines or other hematopoietic factors, isolated RR1 protein or ligand may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering isolated RR1 protein or ligand in combination with cytokine (s), lymphokine(s), other hematopoietic factor(s), thrombolytic or anti-thrombotic factors.

Administration of isolated RR1 protein or ligand used in the pharmaceutical composition or to practice the method of the present invention can be carried out in a variety of conventional ways, such as oral ingestion, inhalation, or cutaneous, subcutaneous, or intravenous injection. Intravenous administration to the patient is preferred.

When a therapeutically effective amount of isolated RR1 protein or ligand is administered orally, isolated RR1 protein or ligand will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% isolated RR1 protein or ligand, and preferably from about 25 to 90% isolated RR1 protein or ligand. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of isolated RR1 protein or ligand, and preferably from about 1 to 50% isolated RR1 protein or ligand.

When a therapeutically effective amount of isolated RR1 protein or ligand is administered by intravenous, cutaneous or subcutaneous injection, isolated RR1 protein or ligand will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to isolated RR1 protein an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additive known to those of skill in the art.

The amount of isolated RR1 protein or ligand in the pharmaceutical composition of the present invention will depend upon the nature and severity of the condition being treated, and on the nature of prior treatments which the patient has undergone. Ultimately, the attending physician will decide the amount of isolated RR1 protein or ligand with which to treat each individual patient. Initially, the attending physician will administer low doses of isolated RR1 protein or ligand and observe the patient's response. Larger doses of isolated RR1 protein or ligand may be administered until the optimal therapeutic effect is obtained for the patient, and at that point the dosage is not generally increased further. It is contemplated that the various pharmaceutical compositions used to practice the method of the present invention should contain about 0.1 µg to about 100 mg of isolated RR1 protein or ligand per kg body weight.

The duration of intravenous therapy using the pharmaceutical composition of the present invention will vary, depending on the severity of the disease being treated and the condition and potential idiosyncratic response of each individual patient. It is contemplated that the duration of each application of the isolated RR1 protein or ligand will be in the range of 12 to 24 hours of continuous intravenous administration. Ultimately the attending physician will decide on the appropriate duration of intravenous therapy using the pharmaceutical composition of the present invention.

Isolated RR1 protein of the invention may also be used to immunize animals to obtain polyclonal and monoclonal antibodies which specifically react with the RR1 protein and which may inhibit ligand binding to the RR1. Such antibodies may be obtained using the entire RR1 protein as an immunogen, or by using fragments of RR1 protein such as the soluble mature RR1 protein. Smaller fragments of the RR1 protein may also be used to immunize animals. The peptide immunogens additionally may contain a cysteine residue at the carboxyl terminus, and are conjugated to a hapten such as keyhole limpet hemocyanin (KLH). Additional peptide immunogens may be generated by replacing tyrosine residues with sulfated tyrosine residues. Methods for synthesizing such peptides are known in the art, for example, as in R. P. Merrifield, J. Amer. Chem. Soc. 85, 2149–2154 (1963); J. L. Krstenansky, et al., FEBS Lett. 211, 10 (1987).

Neutralizing or non-neutralizing antibodies (preferably monoclonal antibodies) binding to RR1 protein or RR1 ligand may also be useful therapeutics for certain tumors and also in the treatment of conditions described above. These neutralizing monoclonal antibodies are capable of blocking the ligand binding to the RR1 protein.

EXAMPLE 1

Isolation of Human RR1 cDNA

Enrichment of human dendritic cells. Human peripheral blood mononuclear cells (PBMC) obtained from a leukopak were separated from the remaining RBCs using Ficoll-Paque. The PBMC were recovered from the interface and washed three times in RPMI supplemented with 10% heat inactivated Fetal Bovine Serum, $5 \times 10^{-5}$ M 2-mercaptoethanol, 100 mM Streptomycin, 100 mM penicillin and 100 mM glutamine (RPMI-10). Following the final wash the cells were resuspended at $2$–$4 \times 10^6$/ml in RPMI-10 and plated into T-150 flasks at 100 ml/flask. The flasks were incubated for two hours at 37° C. in an atmosphere of 5% $CO_2$ and 95% air. Following this incubation the nonadherent cells were removed by washing twice with RPMI-10. Fifty milliliters of RPMI-10 supplemented with 50 ng/ml of hGM-CSF (Genetics Institute) and 30 U/ml hIL-4 (Genzyme) was added to each flask of adherent cells and the cultures were incubated for 18 hours at 37° C. in an atmosphere of 5% $CO_2$ and 95% air. The media and the overnight nonadherent cells were recovered, transferred to new flasks and incubated feeding with fresh GM-CSF and IL-4 every three days for 16 days at 37° C. in an atmosphere of 5% $CO_2$ and 95% air.

Differential mRNA display. THP-1 cells were grown in RPMI-10. Total RNA was isolated from either THP-1 cells or enriched dendritic cells (EDC) with RNAzol™ (Cinna Scientific) using the manufacturer's suggested protocol. cDNA was synthesized from 1 ug of total RNA using the Superscript RT cDNA Synthesis kit (Gibco/BRL) following the manufacturer's suggested protocol with the substitution of $T_{12}MC$ (TTTTTTTTTTTT[G,C,A]C, SEQ ID NO:3) primer for the poly-T primer and the addition of 10 U of RNAse One (Promega) in a total volume of 20 µl. A PCR reaction was set up in duplicate as described by (Pardee, et al., Science 257:967–971 (1992)) with 2.0 µl of the cDNA from either the THP-1 or EDC cells, 2.5 µM $T_{12}MC$, 2.0 µM AU3 (AUUUAUUUAUUUA, SEQ ID NO:4), 2.0 µM dNTP, 0.5 µM $^{35}$S-dATP, in a total volume of 20 µl of PCR buffer I (Perkin Elmer). The reaction volume was overlayed with 20 µl of mineral oil and incubated for 40 cycles of 94° C. for 30 seconds, 42° C. for one minute, and 72° C. for 30 seconds; followed by one cycle of 72° C. for five minutes. The aqueous phase was extracted with chloroform and 5 µl was added to 2 µl formamide loading buffer, heated to 95° C. for five minutes, run on a 6% acrylamide/urea denaturing gel. The gel was dried and exposed to X-OMAT AR film (Kodak) for 18 hours. Visualized bands were cut out of the gel and extracted with 100 µl of $H_2O$ by boiling for 10 minutes and then ethanol precipitating in the presence of glycogen. The precipitate was resuspended in 10 µl of $H_2O$ and 4.0 µl was used to reamplify by PCR using the above described conditions with the exception of an increase of dNTP from 2.0 µM to 20 µM and the elimination of $^{35}$S-dATP. The PCR product was cloned into the pCR II vector using the TA Cloning kit (Invitrogen). The clones were analyzed by EcoRI digestion of mini prep DNA. Those clones displaying inserts of the appropriate size were sequenced using Sequenase Sequencing kit (United States Biochemical). The sequenced clones were checked against the GENBANK database using FASTA (GCG). A 151 bp clone was identified as novel and found to contain the motif TTATTTAAA (SEQ ID NO:5) which has been associated with mRNA destabilization (Lagnado, et al., Mol. Cell. Biol. 14:7984–7995 (1994)).

Cloning of the full length gene. A 141 bp probe of the 151 bp clone was amplified by PCR using GTCAGAAAAATTT-TAATTTAGG (SEQ ID NO:6) and AAATACAGTTTGCT-TATGAAAG (SEQ ID NO:7) as the 5' and 3' primers, respectively. Using this probe $1 \times 10^6$ clones from a Uni-ZAP XR human fetal spleen library (Stratagene) were screened. Four plaques were identified which contained sequences which hybridized with the PCR probe. The size of the inserts was analyzed by amplification by PCR using phage specific primers. The phage containing the largest insert (identified as clones hRR1) was excised using the manufacturer's suggested method. The complete sequences of the insert was determined by dideoxy chain termination DNA sequencing. The sequence was compared to the GENBANK database using FASTA on the entire sequence and BLASTX on the deduced open reading frame. It is believed that clone hRR1 was actually a false positive in this screening procedure for the full length form of the 151 bp clone.

Clone hRR1 was deposited with ATCC on Jun. 27, 1995 as accession number ATCC 69855.

Analysis of the sequence. Using BLASTX on the deduced open reading frame of the full length sequence of hRR1 a region (AA 370–555) was found which showed significant identity to several thyroid/retinoid/steroid receptor gene superfamily members. When compared to the *Chironomus tentans* ecdysone receptor a 70% (66/94) identity was found and compared to the *Homo sapiens* retinoic acid receptor-gamma a 59% (39/66) identity was found. This region of identity corresponds to the identifying region of these family members and is the most conserved region among members of this superfamily (Evans, Science 240:889–895 (1988)). This domain is a "zinc finger" structure responsible for the DNA binding properties of these receptors. When the cysteine residues required for the Zn binding necessary to maintain the three dimensional structure of this region were investigated, all were found to be retained in the sequence of hRR1 (Luisi, et al., Nature 352:497–505 (1991)). Further sequence comparisons of other areas of hRR1 enable the assignment of the other structural domains common to these family members although the homology was lower than that found in the DNA binding domain.

EXAMPLE 2

Transcription and Translation of hRR1

DNA from the expression plasmid pcDNA3 (Invitrogen) was digested overnight with EcoRV at 37° C. The digested plasmid was separated from undigested DNA using a 1.0% agarose gel. The EcoRV fragment was cut from the gel, isolated by electroelution and the concentration determined by agarose gel electrophoresis.

hRR1 was isolated by double digesting a pBluescript phagemid containing the full length hRR1 clone with Bfa I and Hae III overnight at 37°. After separation on a 1.0% agarose gel, the band (NA 138–1803) containing the hRR1 coding region was electroeluted from the gel. The ends were filled in using Pfu DNA polymerase for 1 hour at 72° C. and the DNA concentration assessed by agarose gel electrophoresis.

The EcoRV fragment of pcDNA3 and the Bfa/Hae fragment of hRR1 were ligated together using T4 ligase overnight at 16° C. A clone of pcDNA3 containing the hRR1 fragment was isolated and the orientation confirmed by restriction digest analysis.

To investigate the production of hRR1 protein, 2 ug of DNA from the pcDNA3 plasmid containing either the hRR1 or no insert was digested with Xba I for 1 hour at 37° C. The product was extracted with phenol/chloroform, the aqueous phase recovered, and 1/10 the volume of $NH_4$Acetate was added. The DNA was precipitated by adding 2.5 volumes of 100% ethanol and chilling on dry ice for 30 minutes. The precipitates were collected by spinning for 30 minutes at 14,500 ×g. After washing in 70% ethanol, the precipitated DNA was dried by vacuum centrifugation and resuspended in 14.5 ul of nuclease-free $H_2O$. Using the TNT Coupled Wheat Germ Extract System (Promega) in vitro transcription and translation was performed following the manufacturer's recommendations including $^{35}S$-Methionine and $^{35}S$-Cysteine (Amersham). The protein products were separated by 12% polyacryamide gel electrophoresis. The radiolabeled bands were detected by autoradiography using ENHANCE (New England Nuclear) after an 18 hour exposure at –70° C. A single band was detected in the reaction containing the hRR1 whereas no equivalent band was found in the reaction containing only the pcDNA3 plasmid (see FIG. 1). This band had an observed molecular weight of 56,000 kDa which corresponds closely to the calculated molecular weight of 54,409 kDa.

All patent and literature references cited herein are incorporated by reference as if fully set forth.

What is claimed is:

1. An isolated RR1 protein comprising an amino acid sequence selected from the group consisting of:
   (a) the amino acid sequence of SEQ ID NO:2;
   (b) the amino acid sequence of SEQ ID NO:2 from amino acids 1 to 126;
   (c) the amino acid sequence of SEQ ID NO:2 from amino acids 127 to 192;
   (d) the amino acid sequence of SEQ ID NO:2 from amino acids 193 to 256; and
   (e) the amino acid sequence of SEQ ID NO:2 from amino acids 257 to 470.

2. The protein of claim 1 comprising the amino acid sequence of SEQ ID NO:2.

3. The protein of claim 1 comprising the sequence from amino acid 1 to 126 of SEQ ID NO:2.

4. The protein of claim 1 comprising the sequence from amino acid 127 to 192 of SEQ ID NO:2.

5. The protein of claim 1 comprising the sequence from amino acid 193 to 256 of SEQ ID NO:2.

6. The protein of claim 1 comprising the sequence from amino acid 257 to 470 of SEQ ID NO:2.

7. A composition comprising an RR1 protein of claim 1 and a pharmaceutically acceptable carrier.

8. An isolated polynucleotide comprising a nucleotide sequence selected from the group consisting of:
   (a) the nucleotide sequence of SEQ ID NO:1 from nucleotide 363 to nucleotide 1778;
   (b) a nucleotide sequence varying from the sequence of the nucleotide sequence specified in (a) as a result of degeneracy of the genetic code; and
   (c) an allelic variant of the nucleotide sequence specified in (a).

9. The polynucleotide of claim 8 wherein said nucleotide sequence encodes for a protein having an activity selected from the group consisting of RR1 DNA-binding activity.

10. The polynucleotide of claim 8 wherein said nucleotide sequence is operably linked to an expression control sequence.

11. The polynucleotide of claim 8 comprising the nucleotide sequence of SEQ ID NO:1 from nucleotide 363 to nucleotide 1778.

12. A polynucleotide encoding the protein of claim 2.

13. A polynucleotide encoding the protein of claim 3.

14. A polynucleotide encoding the protein of claim 4.

15. A polynucleotide encoding the protein of claim 5.

16. A host cell transformed with the polynucleotide of claim 10.

17. The host cell of claim 16, wherein said cell is a mammalian cell.

18. A process for producing an RR1 protein, said process comprising:
   (a) growing a culture of the host cell of claim 16 in a suitable culture medium; and
   (b) purifying the RR1 protein from the culture.

19. An RR1 protein produced according to the process of claim 18.

20. A polynucleotide encoding the protein of claim 6.

* * * * *